(12) United States Patent
Gerlitz et al.

(10) Patent No.: US 10,588,552 B2
(45) Date of Patent: *Mar. 17, 2020

(54) SUBSTANCE CONCENTRATION ANALYSIS METHODS AND APPARATUSES

(71) Applicant: GlucoVista Inc., Fairfield, NJ (US)

(72) Inventors: Yonatan Gerlitz, Herzliya (IL); Efraim Landa, Fairfield, NJ (US); Alexander Ostritsky, Rishon Le Zion (IL)

(73) Assignee: GlucoVista Inc., Fairfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/653,428

(22) Filed: Jul. 18, 2017

(65) Prior Publication Data

US 2017/0311854 A1 Nov. 2, 2017

Related U.S. Application Data

(63) Continuation-in-part of application No. 14/745,180, filed on Jun. 19, 2015.
(Continued)

(51) Int. Cl.
*A61B 5/1455* (2006.01)
*A61B 5/145* (2006.01)
(Continued)

(52) U.S. Cl.
CPC ........ *A61B 5/14532* (2013.01); *A61B 5/0075* (2013.01); *A61B 5/1455* (2013.01);
(Continued)

(58) Field of Classification Search
None
See application file for complete search history.

(56) References Cited

U.S. PATENT DOCUMENTS 5,900,632 A * 5/1999 Sterling ................. G01N 21/71
250/252.1
6,198,949 B1 3/2001 Braig et al.
(Continued)

FOREIGN PATENT DOCUMENTS

| WO | 0053086 A1 | 9/2000 |
|---|---|---|
| WO | WO20030045233 A1 | 6/2003 |
| WO | 2012037029 A1 | 3/2012 |

OTHER PUBLICATIONS

International Searching Authority; International Search Report and Written Opinion for Internation Application No. PCT/US2017/042675 dated Nov. 2, 2017.
(Continued)

*Primary Examiner* — Eric F Winakur
*Assistant Examiner* — Marjan Fardanesh
(74) *Attorney, Agent, or Firm* — Randall Danskin P.S.

(57) ABSTRACT

A substance concentration analysis method includes calculating a difference for the particular time between a first measured amount of mid-infrared (MIR) radiation absorbed by or emitted from a body in a first wavelength and a second measured amount of MIR radiation absorbed by or emitted from the body in a second wavelength, calculating a quotient including a dividend based on the difference divided by a divisor based on a dT/dt value, and calculating the concentration of the substance in the body based on a correlation with the quotient.

20 Claims, 6 Drawing Sheets

Related U.S. Application Data (60) Provisional application No. 62/363,721, filed on Jul. 18, 2016, provisional application No. 62/028,884, filed on Jul. 25, 2014, provisional application No. 62/014,518, filed on Jun. 19, 2014.

(51) Int. Cl.
*A61B 5/00* (2006.01)
*G01N 21/01* (2006.01)
*G01N 21/86* (2006.01)
*G01N 35/00* (2006.01)
*A61B 5/1491* (2006.01)
*A61B 5/01* (2006.01)

(52) U.S. Cl.
CPC ........... *A61B 5/1491* (2013.01); *G01N 21/01* (2013.01); *G01N 21/86* (2013.01); *G01N 35/00029* (2013.01); *A61B 5/00* (2013.01); *A61B 5/01* (2013.01); *A61B 5/7203* (2013.01); *G01N 35/00* (2013.01); *G01N 2035/00356* (2013.01)

(56) References Cited

U.S. PATENT DOCUMENTS

| | | |
|---|---|---|
| 6,662,030 B2 | 12/2003 | Khalil et al. |
| 2009/0259407 A1 | 10/2009 | Gerlitz |
| 2010/0016689 A1 | 1/2010 | Kanayama et al. |
| 2010/0312314 A1 | 12/2010 | Ice et al. |
| 2011/0004080 A1 | 1/2011 | Gerlitz |
| 2011/0098542 A1 | 4/2011 | Gerlitz |
| 2012/0197622 A1 | 8/2012 | Jain |
| 2014/0371552 A1 | 12/2014 | Gerlitz |
| 2015/0366490 A1 | 12/2015 | Gerlitz et al. |

OTHER PUBLICATIONS

Yeh S-J et al: "Monitoring Blood Glucose Changes in Cutaneous Tissue by Temperature-Modulated Localized Reflectance Measurements", Clinical Chemistry, Washington, DC vol. 49, No. 6, pp. 924-934 Jun. 1, 2003.
International Searching Authority; International Search Report and Written Opinion for Application No. PCT/US2015/036786 dated Sep. 15, 2015.

\* cited by examiner

SUBSTANCE CONCENTRATION ANALYSIS METHODS AND APPARATUSES

CROSS REFERENCE TO RELATED APPLICATIONS

This application claims the benefit of priority under 35 U.S.C. § 119 to U.S. Provisional Patent Application No. 62/363,721, filed on Jul. 18, 2016 and entitled "Method for Non-Invasive Analysis of a Substance Concentration Within a Body," which is herein incorporated by reference in its entirety. This application is also a continuation-in-part of U.S. patent application Ser. No. 14/745,180, filed on Jun. 19, 2015 and entitled "Substance Concentration Monitoring Apparatuses and Methods," which claims the benefit of priority under 35 U.S.C. § 119 to U.S. Provisional Patent Application No. 62/014,518, filed on Jun. 19, 2014 and entitled "Continuous Noninvasive Glucometer" and to U.S. Provisional Patent Application No. 62/028,884, filed on Jul. 25, 2014 and entitled "Continuous Noninvasive Glucometer," the contents of each of which are herein incorporated by reference in their entirety.

BACKGROUND

Spectroscopic techniques using infrared ("IR") radiation are known in the prior art and have been widely used for non-invasive measurement of the concentration of substances of interest in a body. One area of particular interest is the use of these techniques for the non-invasive measurement of the concentration of glucose and other constituents of the human bloodstream. Several patents and patent applications disclose methods to non-invasively measure the concentration of a substance, such as glucose, for example, in the bloodstream using infrared detection systems and methods.

U.S. patent application Ser. No. 12/883,063, filed Sep. 15, 2010 and entitled "Method for non-invasive analysis of a substance concentration within a body," describes methods of measuring a concentration of a substance, such as glucose, in a body. The described methods include changing the temperature of the surface of a body from a first temperature to a second temperature, then changing the temperature of the surface of the body from the second temperature back to the first temperature. The method includes measuring a first amount of infrared ("IR") radiation absorbed by or emitted from the surface of the body in a first wavelength band and a second amount of IR radiation absorbed by or emitted from the surface of the body in a second wavelength band at predetermined time intervals. The measurements occur during the time period that the temperature of the surface of the body changes from the second temperature back to the first temperature. A concentration of the substance may be determined based on the measurements. The contents of U.S. patent application Ser. No. 12/883,063 are hereby incorporated by reference in their entirety.

SUMMARY

One substance concentration analysis method includes calculating a dT/dt value for a particular time for a temperature derivative with respect to time (dT/dt) of a function for a measured surface temperature (T) of a body that varies with time (t), calculating a difference for the particular time between a first measured amount of mid-infrared (MIR) radiation absorbed by or emitted from a body in a first wavelength and a second measured amount of MIR radiation absorbed by or emitted from the body in a second wavelength, calculating a quotient including a dividend based on the difference divided by a divisor based on the dT/dt value, and calculating the concentration of the substance in the body based on a correlation with the quotient and outputting the concentration to a user.

Another substance concentration analysis method includes inducing a change in a temperature (T) of a surface of a body over time (t) by heating or cooling with an element according to a signal received by the element, then allowing temperature recovery of the surface and yielding a function for temperature (T) that varies with time (t) during the temperature recovery so as to exhibit a temperature derivative with respect to time (dT/dt). The method includes measuring the temperature (T) of the surface of the body over time (t) during the temperature recovery and calculating the dT/dt, measuring mid-infrared (MIR) radiation absorbed by or emitted from the body during the temperature recovery while the surface of the body exhibits the dT/dt, calculating a measured value based on the MIR radiation measurement and on the dT/dt, and calculating the concentration of the substance in the body based on a correlation with the measured value.

One substance concentration analysis apparatus configured to implement any of the methods herein includes a housing, at least one MIR detector attached to the housing, a ring-shaped heating and/or cooling element attached to the housing, a processor controlling the MIR detector and the ring-shaped heating and/or cooling element, and a transmission window structure in direct thermal communication with the ring-shaped heating and/or cooling element and attached to the housing such that a line of sight of the MIR detector passes through the transmission window structure.

Another substance concentration analysis apparatus includes a housing, at least one MIR detector attached to the housing, a ring-shaped heating and/or cooling element attached to the housing, and a thermally conductive ring in thermal communication with the ring-shaped heating and/or cooling element. The apparatus includes a transmission window structure attached to the housing such that a line of sight of the MIR detector passes through the transmission window structure, a surface of the transmission window structure, and a surface of the thermally conductive ring being aligned along a same plane outside the housing.

BRIEF DESCRIPTION OF THE DRAWINGS

Some embodiments are described below with reference to the following accompanying drawings.

DETAILED DESCRIPTION

Disclosed herein are embodiments of systems and methods to non-invasively monitor a concentration of a substance of interest within a body. The monitoring may occur continuously or non-continuously. As an example, the embodiments described herein may be used to continuously monitor a concentration of glucose in a person's blood. Some of the embodiments described herein may be worn for periods of time that range from several minutes to days. As another example, the embodiments herein may be used to analyze a concentration of glucose in a person's blood at a particular time. The infrared measurements may be taken in the mid infrared (MIR) range, where infrared spectra exhibit wavelengths of about 6 to about 15 micrometers ($\mu$m).

The photonic processes of absorption/emission are much faster (several orders of magnitude) than the other methods of heat transfer. Therefore, the deviation of the skin's absorption/emission from the black body emission due to molecular spectral absorption/emission is proportional to the derivative of the temperature change of the skin in time, dT/dt. As a result, the ratio of or the difference between two signals (for example, one signal where glucose has an emission/absorption signal and another signal where glucose has no, or marginal, emission/absorption signal) is also proportional to dT/dt.

Figure 8:
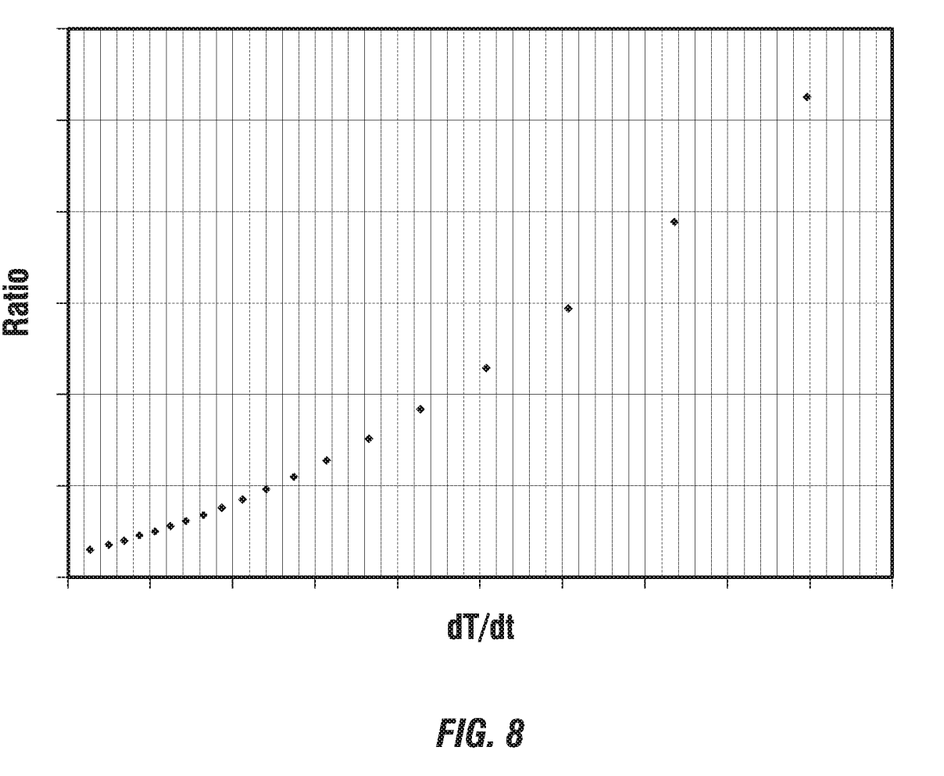
Referring to FIG. 8, a hypothetical graph is shown of a ratio of two signals in a first wavelength with glucose emission/absorption and a second wavelength with no, or marginal, glucose emission/absorption versus dT/dt.

The relationship between dT/dt and the ratio or difference may be described with a function for dT/dt (see FIG. 8). The existence of the function thus permits statistically smoothing measured ratio or difference values before correlating the ratio or difference to the blood glucose concentration level. Known algorithms for smoothing data may be applied to data points containing a ratio or difference value and a dT/dt value calculated from measurements. Possible examples include algorithms provided in EXCEL available from Microsoft Corp. in Kirkland, Wash. and provided in MAT-LAB available from The MathWorks, Inc. in Natick, Mass. Utilizing this correction increases accuracy of the correlation of the ratio or difference to the blood glucose concentration level.

Figure 1:
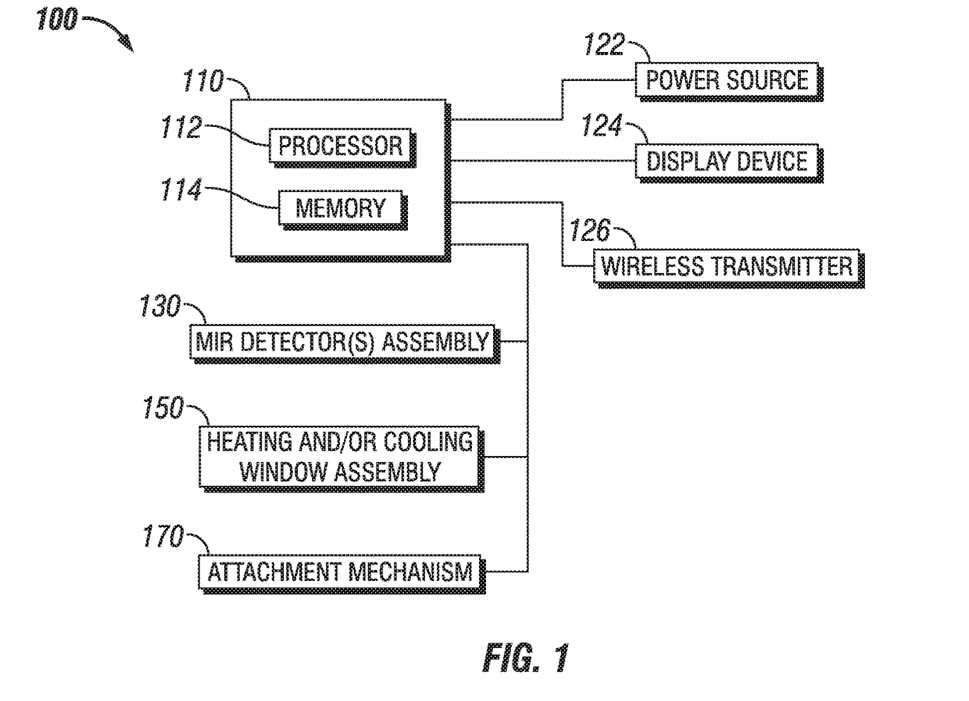
Referring to FIG. 1, a block diagram of an embodiment of a wearable system for continuously monitoring a concentration of a substance in a body is depicted and generally designated 100.

Referring to FIG. 1, a block diagram of an embodiment of a wearable system for continuously or non-continuously monitoring a concentration of a substance in a body is depicted and generally designated 100. The system 100 may include a controller 110, a power source 122, a display device 124, a wireless transmitter 126, a mid-infrared (MIR) detector assembly 130, a heating and/or cooling window assembly 150, and an attachment mechanism 170. The MIR detector 130 may include a preassembled sensor and an optical element (not shown). For example, the optical element may include a lens, and may focus raw IR radiation on the sensor in order to detect the radiation. In other embodiments, the optical element may be a window.

The controller may include a processor 112 and a memory 114. The processor 112 may include any circuitry capable of receiving and processing data. For example, the processor 112 may include a microprocessor, a microcontroller, a peripheral interface controller (PIC), a digital signal processor (DSP), another type of processing element, or any combination thereof.

The memory 114 may include one or more registers, cache memory, random access memory (RAM), read only memory (ROM), solid state memory, magnetic disc memory, another type of volatile or non-volatile memory, or any combination thereof.

One or both of the processor 112 and the memory 114 may be implemented using circuit logic, an application specific integrated circuit (ASIC), a field programmable gate array (FPGA), another type of circuit implementation platform, or any combination thereof.

The memory 114 may be accessible to the processor 112 to enable the processor 112 to retrieve data from the memory 114 and to store data at the memory 114. To illustrate, the memory 114 may include a processor readable medium that may store instructions that, when executed by the processor, cause the processor to perform operations as described herein.

The power source 122 may provide power to the controller 110, the display device 124, the wireless transmitter 126, the MIR detector assembly 130, the heating and/or cooling window assembly 150, or to any subset thereof. The power source 122 may be lightweight and portable to enable the system 100 to be worn on a body without restricting movement of the body. The power source 122 may further hold a charge for extended durations to enable long term portability. For example, the power source 122 may be capable of powering the system 100 for one or more days without being recharged. In an embodiment, the power source 122 includes a rechargeable lithium ion battery pack.

The display device 124 may include any device capable of outputting visual or audio signals to a user of the system 100. For example, the display device may include a liquid crystal diode (LCD) screen, a buzzer, another type of visual or audio output device, or any combination thereof. Although FIG. 1 depicts the system 100 as including the display device 124, in some embodiments, the system 100 may omit the display device 124. As an example, in some embodiments, the system 100 may rely on a wireless transmission to a remote device to generate user outputs.

The wireless transmitter 126 may include any device capable of transmitting information to a remote device. The remote device may include a mobile telephone, a portable music player, a tablet computer, a laptop computer, another type of computing device, or combinations thereof. In some embodiments, the wireless transmitter may communicate with the remote device via a network. For example, the network may include a point-to-point network, a cellular network, a local area network, a wide area network, another type of digital network, or combinations thereof. Although FIG. 1 depicts the system 100 as including the wireless transmitter 126, in some embodiments, the system 100 may omit the wireless transmitter 126. As an example, in some embodiments, the system 100 may rely on the display device 124 to generate user outputs instead of the wireless transmitter 126.

The MIR detector assembly 130 may include devices capable of detecting MIR emission and/or absorption within one or more wavelength bands. For example, the MIR detector assembly 130 may detect MIR emission and/or absorption in a first wavelength band where a substance of interest, e.g., glucose, affects the MIR emission and/or absorption and may also detect MIR emission and/or absorption in a second wavelength band where the substance of interest has no or negligible effect on the MIR emission and/or absorption. The first wavelength band may be referred to as a peak wavelength band and the second wavelength band may be referred to as a reference wavelength band. For example, for glucose, the first wavelength band may be about 9.3 µm to about 9.9 µm. For glucose, the second wavelength band may be about 10.5 µm to about 15 µm. The MIR detector assembly 130 may be further configured to measure the MIR emission and/or absorption of one or more blackbody devices, as described further herein. Embodiments of the MIR detector assembly 130 are described further herein.

The heating and/or cooling window assembly 150 may include devices for heating and/or cooling. The heating and/or cooling window assembly 150 may also include at least one surface that is transparent to MIR radiation to pass the MIR radiation from a body to the MIR detector assembly 130. Passing the MIR radiation may occur at the same time that heating and/or cooling is performed. An embodiment of the heating and/or cooling assembly 150 is further described herein.

The attachment mechanism 170 may include any mechanism capable of attaching one or more components of the system 100 to a body. For example, the attachment mechanism may include a buckle, a hook and loop fastener, a snap, another type of attachment device, or combinations thereof. When the attachment mechanism 170 attaches the system 100 to the body, the system 100 may be configured to ensure contact between the heating and/or cooling window assembly 150 and the body. The attachment mechanism 170 may enable the contact to remain for long durations so the system 100 may be worn on the body.

During operation, the system 100 may continue to be worn on a body for an extended duration of time. For example, the system 100 may be worn for more than 30 minutes, more than one hour, more than 5 hours, or for one or more days. During the duration of time, the attachment mechanism 170 may hold the heating and/or cooling window assembly 150 in contact with the body.

The MIR detector assembly 130 may take or otherwise generate a plurality of MIR measurement sets over the duration of time that the system 100 is worn on the body. The plurality of MIR measurements may be taken without removing the wearable apparatus from the body. Each MIR measurement set may include a first MIR measurement of the body at the peak wavelength band, where a substance of interest has an effect on MIR emission and/or absorption, and a second MIR measurement at a reference wavelength band, where the substance has no or negligible effect on MIR emission and/or absorption. In some embodiments, each measurement set may further include a MIR measurement of one or more blackbody devices within one or both of the wavelength bands.

The MIR measurement sets may be taken through the heating and/or cooling window assembly 150. For example, MIR radiation from the body may pass through a portion of the heating and/or cooling window assembly to the MIR detector assembly 130 to be measured.

While the plurality of MIR measurement sets are being recorded, the heating and/or cooling window assembly may heat and or cool a surface of the body. In some embodiments, the heating and/or cooling window assembly may change a temperature of the body according to a periodic signal received from the controller 110. Each measurement set taken by the system 100 may correspond to a respective period of the periodic signal. Further, each measurement set may be taken during a portion of the periodic signal where the rate of change in temperature of the heating and/or cooling window assembly or of the surface the body is constant. In some embodiments, a period of the periodic signal is about 60 seconds. The periodic signal may be configured to produce a periodic temperature pattern that correspond to a square wave, a triangle wave, a sinusoidal wave, or combinations thereof. Examples of the periodic signal and a resulting periodic change in temperature are described further with reference to FIGS. 7A and 7B.

Figure 7A:
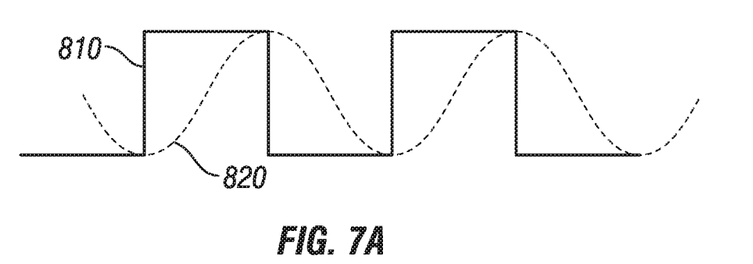
Referring to FIGS. 7A and 7B, an embodiment of periodic signals and corresponding periodic temperature changes are depicted.
Figure 7B:
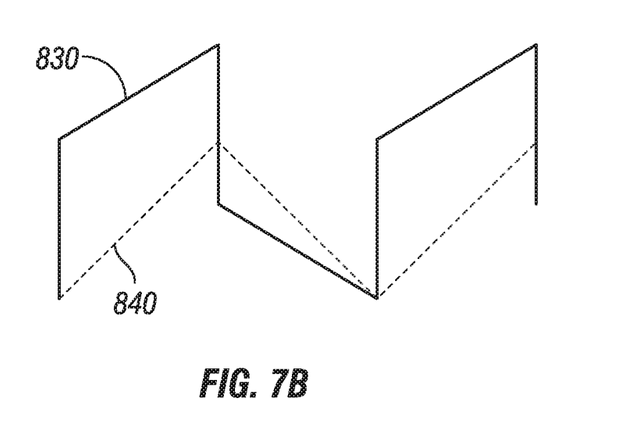

Referring to FIGS. 7A and 7B, an embodiment of periodic signals and corresponding periodic temperature changes are depicted. FIG. 7A depicts a square signal wave 810. When the square signal wave 810 is applied to a heating and/or cooling device, it may result in a sinusoidal temperature wave 820 at the surface of the body. FIG. 7B depicts a signal wave 830. When the signal wave 830 is applied to a heating and/or cooling device, it may result in a triangular temperature wave 840 at the surface of the body. Measurement sets, as described herein, may advantageously be taken during portions of the triangular temperature fluctuation 840 that exhibit a substantially constant rate of temperature change. For example, measurements may be taken when the slope of the triangular temperature fluctuation, such as dT/dt, is approximately constant or, preferably, actually constant.

Referring to either of FIGS. 7A and 7B, a measurement may be taken during a positive dT/dt (where the temperature has a positive slope over time) and another measurement may be taken during a negative dT/dt (where the temperature has a negative slope over time) at the same temperature T. The measurements may be used to isolate a part of the measurement that is f(dT/dt), which corresponds to the glucose emission/absorption band.

MIR radiation emitted from the human body has two major contributors to the MIR signal measured in a band where glucose has peak emission/absorption. First is the normal black body emission which is correlated to the 4th power of temperature ($T^4$). The second contributor is glucose spectral emission/absorption. In cases where the measured volume is approximately in thermal equilibrium, the glucose emission/absorption will approach zero, due to the fact that in thermal equilibrium the number of molecules that emit photons will be close to the number of molecules that absorb photons.

In order to create a measurable signal of glucose emission/absorption, the body matrix is taken out of thermal equilibrium. Furthermore, the photonic relaxation is much faster than any other phenomenon of heat transfer. So, if we take the body matrix out of thermal equilibrium we can expect a short signal from glucose that will disappear once the system returns to thermal equilibrium. In order to create a continuous measurable signal from glucose molecules, we have to create continuous change of the body matrix temperature, so that thermal equilibrium is not reached.

The mathematical representation of emission/absorption due to continuous temperature change will be:

$$M = BB_R \pm f\left(\frac{dT}{dt}\right) * f(N) \pm p \pm k \qquad \text{(Equation 1)}$$

where M is a measured signal, $BB_r$ is a Black Body radiation, f(dT/dt) is a function of the temperature derivative over time, f(N) is a function of the number of glucose molecules in the measured volume, k is a constant, and p is a perturbation, emission or absorption of other substances.

First, we can replace N with:

$$N = V * C' \qquad \text{(Equation 2)}$$

where V is a measured volume that is a constant of the apparatus used and C' is the concentration of glucose in this volume (for example, corresponding to tissue at a particular test site of the body). We denote this concentration as C' as to not be confused with the concentration in the blood (C). We expect C' and C to be highly correlated.

By replacing V with k1 and moving it outside the function we now have:

$$M = BB_R \pm k1 * f\left(\frac{dT}{dt}\right) * f(C') \pm p \pm k \quad \text{(Equation 3)}$$

Note that f(dT/dt) is normalized such that it will be between 0 and 1, which will represent the relative number of molecules that we take out of Boltzmann equilibrium (based on the Boltzmann equation). For example, the Boltzmann equation may describe the change of a macroscopic quantity in a thermodynamic system. Being removed from Boltzmann equilibrium may alter the emission and/or absorption of the molecules and, as such, may have an impact on the macroscopic emission and/or absorption of the body. These molecules will be the population that emits or absorbs photons (depending on the stimulation) and will be a fraction of the total number of molecules (C').

In a first embodiment, the measured volume may be alternately stimulated with heating and cooling. In a second embodiment, the measured volume may be stimulated in one direction and then emission/absorption measured as the volume returns to thermal equilibrium. For the first embodiment, we can separate the heating portion from the cooling portion of stimulation using the equation above to represent measured signal for each portion.

As such we have:

$$M1 = BB_R + k1 * f\left(\frac{dT}{dt}\right) * f(C') \pm p \pm k \quad \text{(Equation 4)}$$

when the volume is being cooled, and:

$$M2 = BB_R - k1 * f\left(\frac{dT}{dt}\right) * f(C') \pm p \pm k \quad \text{(Equation 5)}$$

when the volume is being heated.

If we choose a point where the temperature is the same in both equations then the Black Body radiation in both equations is the same. Subtracting these equations results in $$M1 - M2 = 2\left(k1 * f\left(\frac{dT}{dt}\right) * f(C') \pm p \pm k\right) \quad \text{(Equation 6)}$$

The device also measures radiation in a reference band (where emission/absorption is negligible for glucose). Using the equation above and a value of 0 for f(C') (because no glucose signal is being emitted) we can subtract two reference measurements at the same temperature to obtain the following equation:

$$R1 - R2 = 2(p + k) \quad \text{(Equation 7)}$$

Further, p1=p2 if all the other material in the measured volume that emits radiation in both wave bands has a flat emission spectrum, which means that the emission or absorption in both wavelengths will be the same as long as dT/dt is kept constant, that is, as long as dT/dt has the same absolute value at the same temperature.

We can then use the combination of the two peak glucose measurements and the combination of the reference glucose measurements to obtain the following formula for a measured value (assuming we measure at the same temperature and keep dT/dt constant across all measurements):

$$(M1 - M2) - (R1 - R2) = 2 * k1 * f\left(\frac{dT}{dt}\right) * f(C') \quad \text{(Equation 8)}$$

where M2 and M1 are peak glucose band measurements, R2 and R1 are reference band measurements, k1 is a constant, f(dT/dt) is a factor for how much the measured volume is stimulated, and f(C') is a function for how many glucose molecules are in the measured volume. In the circumstance where f(dT/dt) is not constant or not sufficiently constant, then the formula may be divided by f(dT/dt) such that f(dT/dt) becomes the denominator in the measured value. As a result, dT/dt at the time of MIR measurement may be included in the measured value The output of this function is correlated to the gold standard blood glucose measurement where f(dT/dt) is a value between 0 and 1 and is selected to best fit the correlation with the test measurement. In one example, Equation 8 may be rewritten as follows:

$$\frac{(M1 - M2) - (R1 - R2)}{2 * k1 * f\left(\frac{dT}{dt}\right)} = f(C') \quad \text{(Equation 9)}$$

to determine a slope value. That is, 2*k1*f(dT/dt) may be considered an x value of a data point and (M1−M2)−(R1−R2) may be considered a y value of the data point. After collecting data points over time, such as two to three minutes, when concentration is stabilized (substantially constant), a best fit data analysis may generate a slope for the (x,y) values. Based on Equation 9, the resulting slope value may be correlated to C'. For example, C' may be correlated to the actual concentration of the substance in the blood.

The controller 110 may generate a consecutive plurality of data parameters indicative of respective concentrations of a substance in the body based on the corresponding plurality of MIR measurement sets as described herein. The plurality of data parameters may then be stored. For example, the plurality of data parameters may be stored at the memory 114, or at another memory of the system 100. In the context of the present document, "continuous" monitoring refers to measuring substance concentration over time while the monitoring apparatus continues to contact the body between consecutive measurements. That is, even though the monitoring apparatus may be programmed to take a measurement at periodic intervals, any interval may be selected. The monitoring apparatus is capable of taking a measurement at any time since it is not removed from contact with the body between consecutive measurements. An operator may program a selected measurement interval. Also, the monitoring apparatus may automatically change measurement intervals, depending on programmed conditions. For example, more frequent measurement may be warranted when concentration approaches a level of concern.

As the system 100 is worn on a body, the concentration of the substance within the body may be continuously monitored by determining whether the substance concentrations or the consecutive plurality of data parameters are within a tolerance. For example, as new data parameters indicative of the concentration of the substance are generated at the processor 112, the new data parameters may be compared to one or more tolerances. Alternatively or additionally, the concentrations may be compared to one or more tolerances. The tolerances may be stored at the memory 114 or elsewhere in the system 100. If the new data parameter or concentration is outside the tolerance, such as less than a lower tolerance or greater than an upper tolerance, a warning output may be generated and sent to the display device. Alternatively or in addition, the warning output may be sent to the wireless transmitter.

The wireless transmitter may be configured to send the warning output to a remote device. The remote device may include a cellular telephone, a tablet, a laptop, or another type of mobile computing device. The warning output may indicate to the remote device to display a warning. The warning output may further indicate to the mobile device to contact an emergency service.

Based on the plurality of data parameters, the processor 112 may calculate a continuous correlation function. Thereafter, the processor 112 may modify at least one of the plurality of data parameters based on the continuous correlation function. For example, as the processor 112 generates new data parameters indicative of a concentration of the substance in the body, the processor 112 may adjust or otherwise modify the new data parameters based on the continuous correlation function. Alternatively, the processor 112 may adjust or modify individual raw MIR measurements as they are received from the MIR detector assembly 130 and use the modified MIR measurements in generating new data parameters indicative of a concentration of the substance. The continuous correlation function may reduce noise and/or measurement variations in the plurality of MIR measurement sets.

To illustrate, the continuous correlation function may correlate between the measurement taken and a "gold standard" blood glucose measurement made at the same time. The function parameters are calibrated for each person. The function may be a polynomial, such as:

$$y = a + bx + cx^2 + dx^3 ex^4 \qquad \text{(Equation 10)}$$

where y is glucose concentration and x is the MIR measurement.

The difference of MIR measurement or ratio of MIR measurement is normalized. Results may be normalized against a blackbody with predetermined specifications and corrected for ambient temperature. The parameters of a-e are determined from a set of calibration measurements.

During continuous measurements, there may be many more measurements (N) and the noise in the correlation function that limits its accuracy may be reduced by $\sqrt{N}$. In addition to the above reduction in noise and increase in accuracy, some embodiments may make use of the parameter of maximum change rate of glucose concentration in human body, which is 4 mg/dL/min. In some embodiments, measurements may be taken every 3 seconds, which means that the maximum change between adjacent measurements of glucose may be less than 0.2 mg/dL.

Given the above, a substance concentration monitoring method includes inducing a periodic change in a temperature (T) of a surface of a body over time (t) using a heating and/or cooling element according to a periodic signal received by the element and yielding a function for temperature (T) that varies with time (t) so as to exhibit a temperature derivative with respect to time (dT/dt) that oscillates periodically. Mid-infrared (MIR) radiation absorbed by or emitted from the body is measured while the surface of the body exhibits the oscillating, periodic dT/dt. The method includes determining a measured value based on the MIR radiation measurements and determining a concentration of a substance in the body based on a correlation with the measured value.

By way of example, the measured value may also be based on the oscillating, periodic dT/dt. Further, the measured value may be correlated with glucose concentration. Measuring IR radiation may include measuring the MIR radiation at a temperature during a positive dT/dt (an upward sloping temperature change) and measuring the MIR radiation at the same temperature during a negative dT/dt (a downward sloping temperature change).

The measurement of IR radiation may include measuring a first MIR radiation at a temperature during a positive dT/dt (an upward sloping temperature change), the measuring occurring within a first wavelength band in which the substance has an effect on MIR emission or absorption. The measurement of IR radiation may also include measuring a first reference MIR radiation at the temperature during the positive dT/dt, the measuring occurring within a second wavelength band in which the substance has no or negligible effect on MIR emission or absorption. The measurement of IR radiation may further include measuring a second MIR radiation at the temperature during a negative dT/dt (a downward sloping temperature change), the measuring occurring within the first wavelength band. The measurement of IR radiation may still further include measuring a second reference IR radiation at the temperature during the negative dT/dt, the measuring occurring within the second wavelength band.

In more detail, determining the measured value may include the first and second MIR radiation measurements and the first and second reference MIR radiation measurements in an equation that yields the measured value. The method may further include generating a correlation of the measured value with the substance concentration. For example, a correlation to invasively measured blood concentrations. Also, dT/dt may be determined at the time the MIR radiation is measured and dT/dt may be included in the measured value that is correlated with the substance concentration.

As will be appreciated, the present method or a similar method, such as otherwise described herein, may be implemented with a substance concentration monitoring apparatus. The apparatus may include a processor, a heating and/or cooling element, an infrared sensor, and a memory accessible to the processor. The memory stores instructions that, when executed by the processor, cause the processor to initiate operations including generating a periodic signal configured to control the heating and/or cooling element and thereby to induce a periodic change in a temperature (T) of a surface of a body over time (t) and to yield a function for temperature (T) that varies with time (t) so as to exhibit a temperature derivative with respect to time (dT/dt) that oscillates periodically. The instructions include collecting data from the infrared sensor while the surface of the body exhibits the oscillating, periodic dT/dt. The data results from a measurement of mid-infrared (MIR) radiation absorbed by or emitted from the body within a first wavelength band in which a substance has an effect on MIR emission or absorption and a measurement of MIR reference radiation absorbed by or emitted from the body within a second wavelength band in which the substance has no or negligible effect on MIR emission or absorption. The instructions include determining a measured value based on the MIR radiation data and the MIR reference radiation data and determining a concentration of the substance in the body based on a correlation with the measured value.

By way of example, the processor operations may further include monitoring the concentration of the substance in the body by determining whether the concentration or the measured value are within a tolerance and generating a warning output when the concentration or the measured value is outside the tolerance. Also, the apparatus may further include a wireless transmitter and the processor operations may further include sending the warning output to a remote device via the wireless transmitter to display a warning. For example, the remote device may include a mobile telephone and the warning output may indicate that the remote device is to contact an emergency service.

The measured value may be additionally based on the oscillating, periodic dT/dt. The measured value may be correlated with glucose concentration. Also, collecting the data from the infrared sensor may include collecting the data at a temperature during a positive dT/dt (an upward sloping temperature change) and collecting the data at the same temperature during a negative dT/dt (a downward sloping temperature change). Determining the measured value may involve including the MIR radiation data and the MIR reference radiation data collected during both the positive and the negative dT/dt in an equation that yields the measured value.

The periodic signal may be configured to produce a constant rate of change in temperature (dT/dt) of the heating and/or cooling element during both the positive and the negative dT/dt. As a result, collecting the data may further include determining dT/dt at the time the MIR radiation is measured and determining the measured value may further involve including dT/dt in the measured value that is correlated with the substance concentration. The periodic signal may be configured to produce a periodic temperature pattern of the heating and/or cooling element that corresponds to a square wave, a triangle wave, a sinusoidal wave, or a combination thereof.

For the second embodiment introduced above, the measured volume may be stimulated in one direction and then emission/absorption measured as the volume returns to thermal equilibrium. That is, the radiation measurement may be non-continuous since it does not occur during both heating and cooling. We start with the measured signal in the band where glucose is present as follows with an expression similar to Equation 3:

$$M = BB_R \pm k1 * f\left(\frac{dT}{dt}\right) * f(C') \pm p\left(\frac{dT}{dt}\right) \pm k \quad \text{(Equation 11)}$$

where:
M is the measured signal in the band with glucose;
f(dT/dt) is a function that gives the fraction of glucose molecules between 0 and 1 that will emit or absorb photons when taken out of Boltzmann equilibrium when the rate of temperature change is dT/dt;
f(C') is the quantity of glucose molecules in the measured volume that we want to correlate with the blood glucose as measured by the known gold standard;
p is the emission of other materials in the sample volume that are also a function of dT/dt; and
k1 and k are constants.

Adapting Equation 11 for a measured signal (M) during heating of skin, which may include rewarming of skin after being cooled, provides:

$$M = BB_R - k1 * f\left(\frac{dT}{dt}\right) * f(C') - p\left(\frac{dT}{dt}\right) + C_0 \quad \text{(Equation 12)}$$

where $C_0$ is a constant. Using Equation 12 and a value of 0 for f(C') (because no glucose signal is being emitted) the measured signal in the reference band is:

$$R = BB_R - p_1\left(\frac{dT}{dt}\right) + C_1 \quad \text{(Equation 13)}$$

where $C_1$ is a constant. Assuming $p_1(dT/dt)=p(dT/dt)$, which means other materials in the sample have a flat emission curve spanning both wave bands, subtracting Equation 12 from Equation 13 yields:

$$R - M = k1 * f\left(\frac{dT}{dt}\right) * f(C') + C_2 \quad \text{(Equation 14)}$$

which can be rewritten as $$f(C') = \frac{R - M - C_2}{k1 * f\left(\frac{dT}{dt}\right)} \quad \text{(Equation 15)}$$

where $C_2$ is a constant. The Equation 15 quotient, when all measurements are normalized to black body calibration and corrected for ambient temperature effects on measurement apparatuses, is correlated with the gold standard for blood glucose.

Sterling, et al (U.S. Pat. No. 5,900,632) describe Thermal Gradient Spectroscopy (TGS) where the external layer of skin is cooled to create a thermal gradient based on skin depth (dT/dx). A method herein is to create a thermal change over time (dT/dt). In Sterling's method, he failed to disclose that in order to measure the concentration of a substance across all layers in the measurement medium, thermal diffusivity ($\alpha$, alpha) must be known very accurately according to the following equation $dT/dt=\alpha d^2T/dx^2$ (which is not possible in a complex matrix like the skin).

TGS, as described in Sterling, is based on measurement during cooling of the skin, while one method herein relies on measurement during natural recovery of skin temperature after cooling (i.e. while the skin is warming). That method herein relies on thermal emission from the upper layer of skin while Sterling relies on the upper layer to be transparent to emission from deeper layers in the skin. In Sterling, heating only happens to enable another cooling cycle.

Furthermore, the measurement cycle in Sterling lasts 0.2 seconds, allowing only one measurement per thermal cycle, while a measurement cycle herein can last up to one minute or more enabling multiple measurements during a thermal cycle. This gives the ability to smooth the data collected in a measurement cycle, resulting in more reliable measurement of concentrations over time. The version of dT/dt herein is longer.

One difference between the methods herein and Sterling is that Sterling is measuring a gradient through the skin matrix (dT/dx), but the present methods measure a response to a change in temperature over time (dT/dt).

One substance concentration analysis method includes calculating a dT/dt value for a particular time for a temperature derivative with respect to time (dT/dt) of a function for a measured surface temperature (T) of a body that varies with time (t), calculating a difference for the particular time between a first measured amount of mid-infrared (MIR) radiation absorbed by or emitted from a body in a first wavelength and a second measured amount of MIR radiation absorbed by or emitted from the body in a second wavelength, calculating a quotient including a dividend based on the difference divided by a divisor based on the dT/dt value, and calculating the concentration of the substance in the body based on a correlation with the quotient and outputting the concentration to a user.

By way of example, the quotient may be correlated with glucose concentration. The divisor may be a value of a function of dT/dt (f(dT/dt)) that yields a fraction of the substance concentration between 0 and 1 that emits or absorbs photons when taken out of Boltzmann equilibrium at the dT/dt value. The calculation of the quotient may include calculating a slope value for a series of (x,y) values in which x values are the divisor and y values are the dividend measured over time while the surface exhibits the dT/dt.

The method may further include measuring the first measured amount of MIR radiation absorbed by or emitted from the body in the first wavelength at the particular time, measuring the second measured amount of MIR radiation absorbed by or emitted from the body in the second wavelength at the particular time, and measuring the measured surface temperature at the particular time. The substance may have an effect on MIR emission or absorption in the first wavelength and have no or negligible effect on MIR emission or absorption in the second wavelength. Measuring the first measured amount, the second measured amount, and the measured surface temperature may occur during a positive dT/dt (an upward sloping temperature change).

The method may further include normalizing the first measured amount and the second measured amount to black body calibration, measuring an ambient temperature at the particular time, and correcting the quotient for ambient temperature effects on a measurement apparatus for the ambient temperature.

Calculating the dT/dt value for the particular time may include measuring the measured surface temperature at each of a plurality of different times including the particular time, curve-fitting the corresponding plurality of measured surface temperatures to obtain the function for temperature (T) of the surface of the body that varies with time (t), including the particular time, differentiating the function for temperature (T) to obtain the temperature derivative with respect to time (dT/dt), and calculating the dT/dt value by evaluating the dT/dt for the particular time.

The method may further include generating a correlation of the substance concentration with the quotient by, for each of a plurality of different times, calculating the dT/dt value and calculating the difference. The method includes statistically smoothing the plurality of differences for the corresponding plurality of dT/dt values to correct the plurality of differences and providing a function of dT/dt (f(dT/dt)) that yields a fraction of the substance concentration between 0 and 1 that emits or absorbs photons when taken out of Boltzmann equilibrium. For each of the plurality of different times, the method includes calculating a f(dT/dt) value by evaluating the f(dT/dt) for the respective dT/dt value and calculating the quotient with the corresponding f(dT/dt) value as the divisor. The method includes correlating the concentration of the substance in the body with the plurality of quotients.

Another substance concentration analysis method includes inducing a change in a temperature (T) of a surface of a body over time (t) by heating or cooling with an element according to a signal received by the element, then allowing temperature recovery of the surface and yielding a function for temperature (T) that varies with time (t) during the temperature recovery so as to exhibit a temperature derivative with respect to time (dT/dt). The method includes measuring the temperature (T) of the surface of the body over time (t) during the temperature recovery and calculating the dT/dt, measuring mid-infrared (MIR) radiation absorbed by or emitted from the body during the temperature recovery while the surface of the body exhibits the dT/dt, calculating a measured value based on the MIR radiation measurement and on the dT/dt, and calculating the concentration of the substance in the body based on a correlation with the measured value.

By way of example, the present method may include the features of the other methods herein. The method may include calculating a dT/dt value for the time the MIR radiation is measured. The allowing of temperature recovery of the surface may occur without the heating or cooling of the element. The measured value may be correlated with glucose concentration. Measuring MIR radiation may include measuring MIR radiation during a positive dT/dt (an upward sloping temperature change), the measuring occurring within a first wavelength band in which the substance has an effect on MIR emission and measuring reference MIR radiation at the temperature during the positive dT/dt, the measuring occurring within a second wavelength band in which the substance has no or negligible effect on MIR emission.

One substance concentration analysis apparatus configured to implement any of the methods herein includes a housing, at least one MIR detector attached to the housing, a ring-shaped heating and/or cooling element attached to the housing, a processor controlling the MIR detector and the ring-shaped heating and/or cooling element, and a transmission window structure in direct thermal communication with the ring-shaped heating and/or cooling element and attached to the housing such that a line of sight of the MIR detector passes through the transmission window structure.

By way of example, present apparatus may include the features discussed herein for other apparatuses. Also, the transmission window structure may exhibit a thermal conductivity greater than 1,000 Watts/meter-Kelvin (W/m-K). While germanium and aluminum discussed above exhibit thermal conductivities of about 50 and 180 W/m-K, respectively, chemical vapor deposited diamond (CVDD) exhibits a thermal conductivity of about 1,800 W/m-K. Using a transmission window structure with the higher thermal conductivity in direct thermal contact with the heating and/or cooling element allows faster heat transfer to skin. Also, temperature distribution across the window is more uniform. These features allow increased accuracy in measurements.

Figure 2:
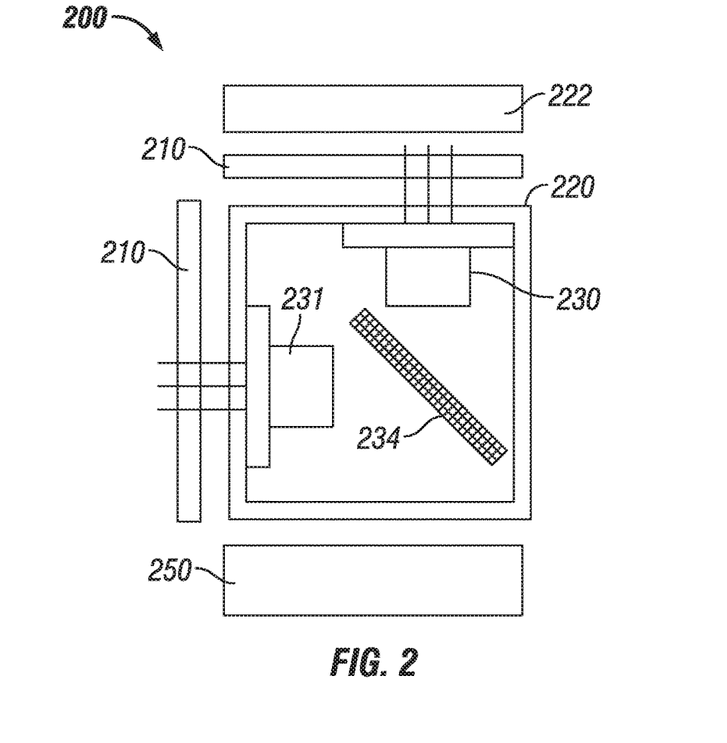
Referring to FIG. 2, an embodiment of a system for continuously monitoring a concentration of a substance in a body is depicted and generally designated 200.

Referring to FIG. 2, an embodiment of a system for continuously or non-continuously monitoring a concentration of a substance in a body is depicted and generally designated 200. The system 200 includes one or more printed circuit boards (PCBs) 210, a housing 220, a battery 222, a first MIR detector 230, a second MIR detector 231, a dichroic beam splitter 234, and a heating and/or cooling window assembly 250. The system 200 may correspond to an apparatus for measuring the concentration of glucose within a body.

The housing 220 may hold the MIR detectors 230-231 and the dichroic beam splitter 234 together in a detection configuration. As such, the housing 220 may serve as an accurate mechanical reference for the positioning of the MIR detectors 230, 231 and the dichroic beam splitter 234. The housing 220 may further be made of a material that conducts heat in order to serve as a heat sink to stabilize the temperatures of the components of the system 200. For example, the housing 220 may be made of aluminum or an aluminum alloy.

The first MIR detector 230 and/or the second MIR detector 231 may include a preassembled sensor and an optical element (not shown). For example, the optical element may include a lens, and may focus raw IR radiation on the sensor in order to detect the radiation. In other embodiments, the optical element may be a window.

The one or more PCBs 210 may include pre-amplifiers, microprocessors, transmitters, receivers, and any other electrical components to implement a controller, e.g., the controller 110. The power source 222 may include a rechargeable lithium ion type battery and may be positioned near the edge of the system 200 to enable easy access for replacement. The heating and/or cooling window assembly 250 may correspond to the heating and/or cooling window assembly 150 and is further described with reference to FIG. 4.

Figure 3:
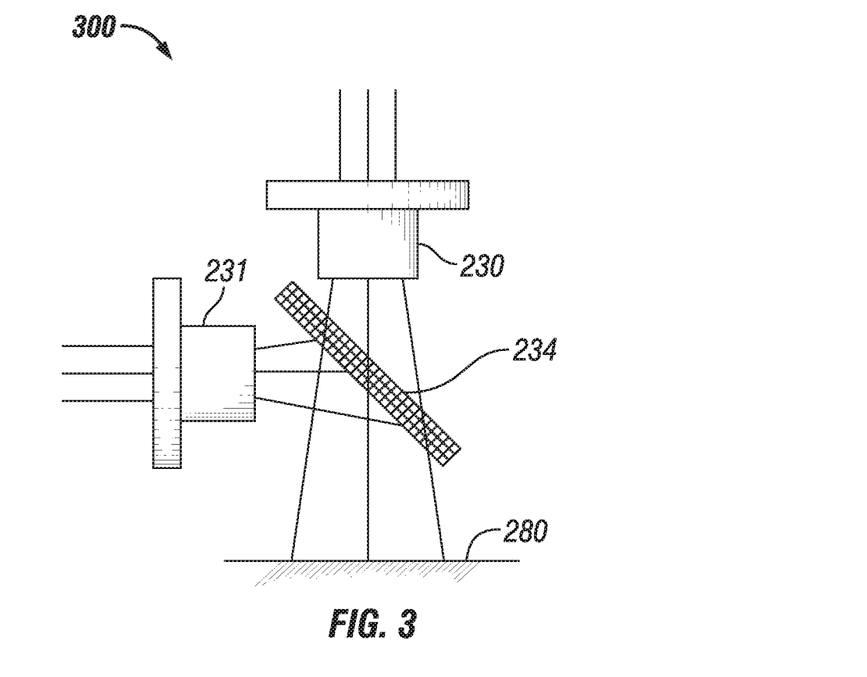
Referring to FIG. 3, an embodiment of a detection configuration is depicted and generally designated 300.

Referring to FIG. 3, an embodiment of a detection configuration is depicted and generally designated 300. For example, FIG. 3 illustrates the configuration of the first MIR detector 230, the second MIR detector 231, and the dichroic beam splitter 234. The first MIR detector 230 and the second MIR detector may include thermopile detectors to detect light within the MIR spectrum.

As depicted in FIG. 3, the first MIR detector 230 may receive IR radiation through the dichroic beam splitter 234 from a measurement area 280. The second MIR detector 231 may receive the same IR radiation through the dichroic beam splitter 234. Both the MIR detectors 230, 231 have a combined field of view after the dichroic beam splitter 234. For example, both the MIR detectors 230, 231 receive radiation from the same measurement area 280.

The first MIR detector 230 may be configured to detect MIR radiation in a first wavelength band (e.g., a peak band). The second MIR detector 231 may be configured to detect MIR radiation in a second wavelength band (e.g., a reference band).

Figure 4:
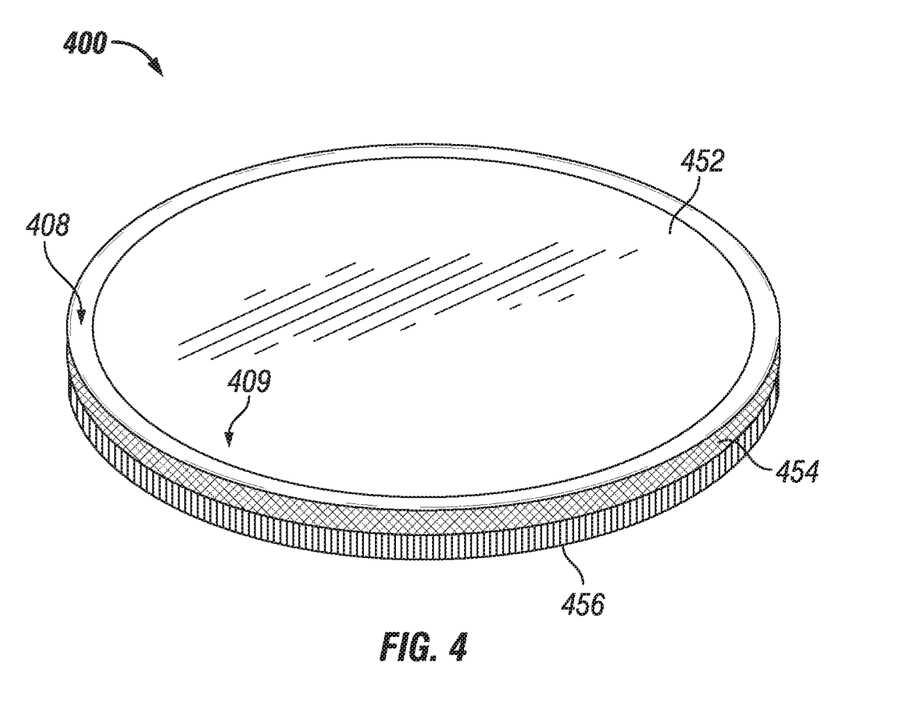
Referring to FIG. 4, an embodiment of a heating and/or cooling window assembly is depicted and generally designated 400.

Referring to FIG. 4, an embodiment of a heating and/or cooling window assembly is depicted and generally designated 400. The assembly 400 includes a transmission window structure 452, a thermally conductive ring 454, and a heating and/or cooling element 456.

The heating and/or cooling element 456 may be ring-shaped and may be attached to the thermally conductive ring 454. In some embodiments, a thermally conductive adhesive is used to attach the heating and/or cooling element 456 to the thermally conductive ring 454. Further, in some embodiments, the heating and/or cooling element 456 is a Peltier element.

The thermally conductive ring 454 may be thicker than the heating and/or cooling element 456 so the internal radius of the thermally conductive ring 454 may be smaller than the internal radius of the heating and/or cooling element 456. In some embodiments, the thermally conductive ring 454 includes aluminum or an aluminum alloy.

The transmission window structure 452 may be attached to the inside of the thermally conductive ring 454. Additionally, the transmission window structure 452 may have an outer down step ring to enable a surface 408 of the thermally conductive ring 454 to be aligned and maintain alignment with a surface 409 of the transmission window structure 452 along a single plane outside the housing 220.

During operation, the surfaces 408, 409 may contact a surface of a body. In some embodiments, the transmission window structure is made of a material that is substantially transparent to light within the MIR range. For example, the transmission window structure may include germanium, silicon, or both.

The heating and/or cooling window assembly 400 may correspond to the assembly 250 and may, in some embodiments, be attached to the housing 220. For example, the heating and/or cooling element 456, the thermally conductive ring 454, or both may be attached to the housing 220. When attached to the housing, the transmission window structure 452 may be positioned such that a line of sight of the MIR detectors 230, 231 passes through the transmission window structure 452.

Figure 5:
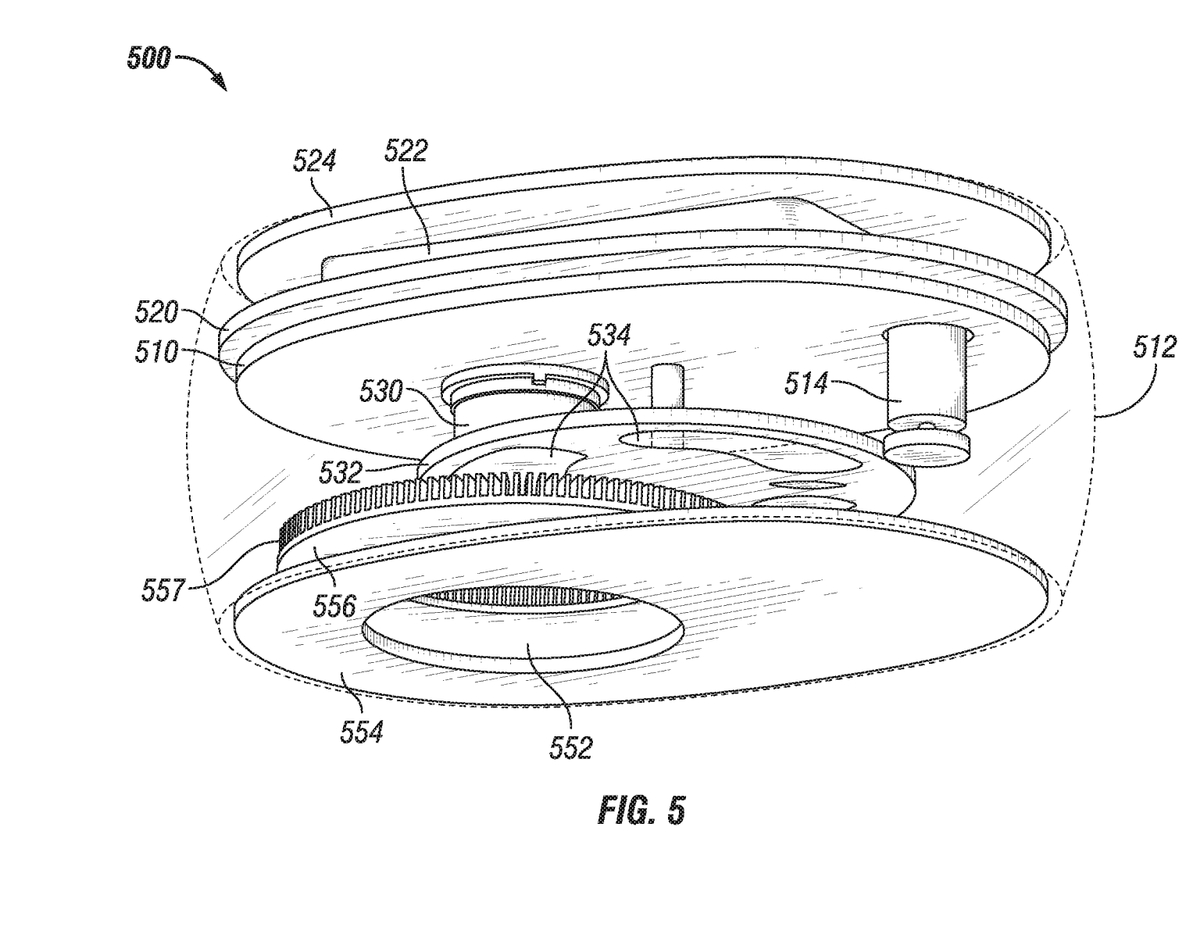
Referring to FIG. 5, an embodiment of a system for continuously monitoring a concentration of a substance in a body is depicted and generally designated 500.

Referring to FIG. 5, an embodiment of a system for continuously or non-continuously monitoring a concentration of a substance in a body is depicted and generally designated 500. The system 500 may include a PCB assembly 510, a MIR detector 530, a filter wheel 532, a heating and/or cooling element 556, a thermally conductive plate 554, and a transmission window structure 552.

The components of the system 500 may be attached, or otherwise held in place, by a metal base 520. The metal base 520 may be made of a thermally conductive material such as aluminum. Metal base plate 520 may further be coupled to a housing 512 that may enclose inner components of the system 500. The components of the system 500 may be powered by a battery 522 held in place by a battery cover 524. In an embodiment, the battery 522 is a rechargeable lithium ion rechargeable type battery.

The PCB assembly 510 may include pre-amplifiers, microprocessors, transmitters, receivers, and any other electrical components to implement a controller, e.g., the controller 110. The MIR detector 530 may be coupled to the PCB assembly and may be positioned above the filter wheel 532. In some embodiments, the MIR detector 530 may include a thermopile sensor as well as a germanium or silicon lens.

The filter wheel 532 may include a plurality of cavities 534 defined therein. The plurality of cavities 534 may hold a plurality of filters. For example, the plurality of cavities 534 may hold a first filter that passes light in a first wavelength band where a substance affects MIR emission or absorption while blocking light that is not within the first wavelength band. The plurality of cavities 534 may further hold a second filter that passes light in a second wavelength band where the substance has no or negligible effect on MIR emission or absorption while blocking light that is not within the second wavelength band.

Additionally, in one or more embodiments, one or more of the plurality of cavities may hold a blackbody device to be used as a reference to stabilize continuous or non-continuous measurements of the MIR detector 530. The filters within the filter wheel 532 may be configured such that a line of sight of the MIR detector 530 is selectively aligned with one of the filters or the blackbody device as the filter wheel 532 rotates. Motor 514 may contact a periphery of filter wheel 532 to rotate it.

The thermally conductive plate 554 may retain the transmission window structure 552. Together, the thermally conductive plate 554 and the transmission window structure 552 may form a surface that may contact a surface of a body during operation of the system 500. To that end, an outer surface of the transmission window structure 552 may be aligned with an outer surface of the thermally conductive plate 554 along a single plane outside the housing 512.

The heating and/or cooling element 556 may have a ring shape and may be coupled to the thermally conductive plate 554. In some embodiments, the thermally conductive plate includes aluminum or an aluminum alloy. The heating and/or cooling element 556 may include an aperture defined therein for MIR light to pass through. A heat sink 557 may be coupled to the heating and/or cooling element to control the temperature and to provide a temperature differential. Further, although not depicted in FIG. 5, in some embodiments, the filter wheel 532 may include fan blades to create an air flow in contact with the heat sink 557. In some embodiments, the heating and/or cooling element may be a Peltier element.

As depicted in FIG. 5, the plurality of cavities 534 of the filter wheel 530 may be have an arcuate shape (e.g., a curved or bow shape). The arcuate shape may enable multiple measurements to be performed through a particular filter or blackbody device held in each cavity of the plurality of cavities 534 before the cavity rotates out of the field of view of the MIR detector 530.

During operation, the filter wheel 532 may rotate at about 20 rotations per minute (RPMs). At this speed, between five and six measurements may be taken through each filter held by the plurality of cavities 534. Further, during the measurements, the thermally conductive plate 552 may cool and/or warm the surface of the body at approximately 60 second cycles and amplitude of approximately 1 degree Kelvin.

Figure 6:
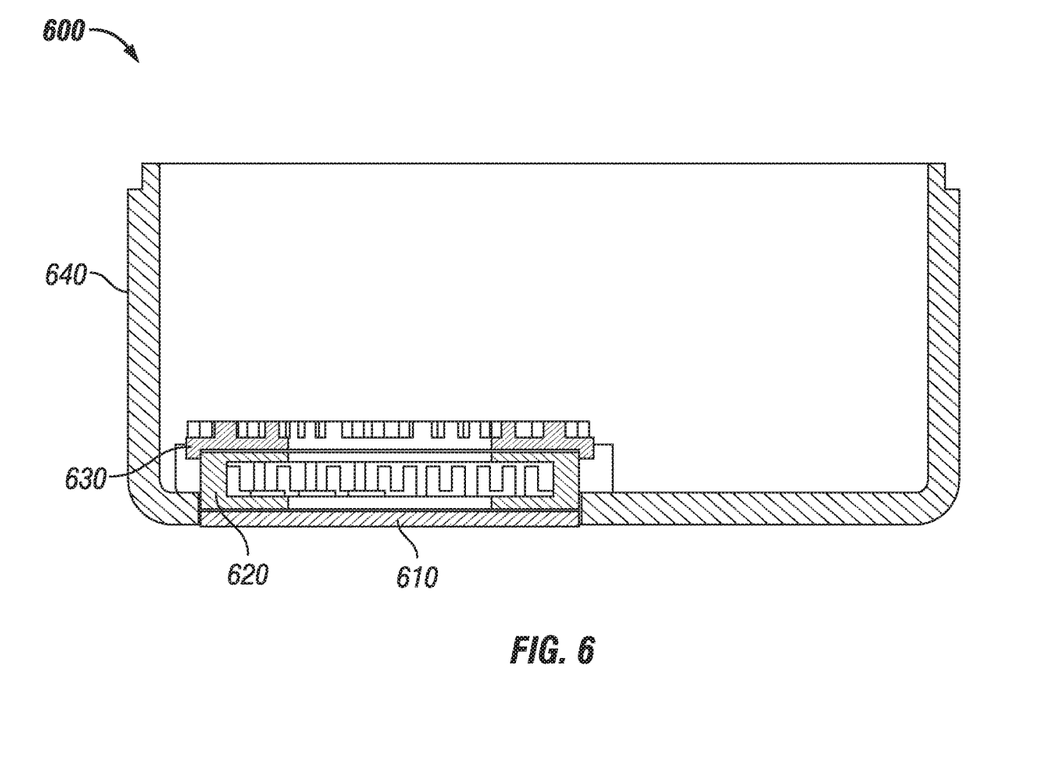
Referring to FIG. 6, an embodiment of another window assembly for the system of FIG. 5 is depicted and generally designated 600.

Referring to FIG. 6, an embodiment of another window assembly for the system of FIG. 5 is depicted and generally designated 600. In this embodiment window 610 is directly attached to the Peltier element 620 without a metal interface. 640 is a thermal insulating plastic case so the heat transfer from the window to other substances, except the skin, is minimal. On the upper part of the Peltier, a heat sink 630 is attached for keeping the temperature of the Peltier's upper plate at room ambient temperature. The heat sink may be made of aluminum or copper.

It will be understood that the details of features described with respect to individual embodiments may be used in like features of the other embodiments described herein as consistent and appropriate even though not expressly indicated in describing the other embodiments.

In compliance with the statute, the embodiments have been described in language more or less specific as to structural and methodical features. It is to be understood, however, that the embodiments are not limited to the specific features shown and described. The embodiments are, therefore, claimed in any of their forms or modifications within the proper scope of the appended claims appropriately interpreted in accordance with the doctrine of equivalents.

TABLE OF REFERENCE NUMERALS FOR FIGURES 100 system
110 controller
112 processor
114 memory

TABLE OF REFERENCE NUMERALS FOR FIGURES 122 power source
124 display device
126 wireless transmitter
130 MIR detector assembly
150 heating/cooling window assembly
170 attachment mechanism
200 system
210 PCB
220 housing
222 battery
230 MIR detector
231 MIR detector
234 beam splitter
250 heating/cooling assembly
280 measurement area
300 configuration
400 window assembly
408 ring surface
409 window surface
452 transmission window structure
454 thermally conductive ring
456 heating/cooling element
500 system
510 PCB assembly
512 housing
514 motor
520 metal base
522 battery
530 MIR detector
532 filter wheel
534 cavities
552 transmission window structure
554 thermally conductive plate
556 heating/cooling element
557 heatsink
600 window assembly
610 window
620 Peltier element
630 heat sink
640 plastic case
810 signal wave
820 temperature wave
830 signal wave
840 temperature wave

What is claimed is:

1. A substance concentration analysis apparatus comprising:
    a housing;
    at least one MIR detector attached to the housing;
    a heating and/or cooling element attached to the housing; and
    a controller configured to control the MIR detector and the heating and/or cooling element, the controller storing instructions that, when executed by the controller, cause the controller to initiate operations including:
        inducing a change in a temperature (T) of a surface of a body over time (t) by heating or cooling with the element according to a signal received by the element, then allowing temperature recovery of the surface and yielding a function for temperature (T) that varies with time (t) during the temperature recovery so as to exhibit a temperature derivative with respect to time (dT/dt);
        measuring the temperature (T) of the surface of the body over time (t) during the temperature recovery and calculating the dT/dt;
        measuring mid-infrared (MIR) radiation absorbed by or emitted from the body during the temperature recovery while the surface of the body exhibits the dT/dt;

calculating a measured value based on the MIR radiation measurement and on the dT/dt; and
calculating the concentration of the substance in the body based on a correlation with the measured value.

2. The apparatus of claim 1, wherein the operations further include:
calculating a dT/dt value for a particular time for a temperature derivative with respect to time (dT/dt) of a function for a measured surface temperature (T) of a body that varies with time (t);
calculating a difference for the particular time between a first measured amount of mid-infrared (MIR) radiation absorbed by or emitted from a body in a first wavelength and a second measured amount of MIR radiation absorbed by or emitted from the body in a second wavelength;
calculating a quotient including a dividend based on the difference divided by a divisor based on the dT/dt value; and
calculating the concentration of the substance in the body based on a correlation with the quotient and outputting the concentration to a user.

3. The apparatus of claim 2, wherein the quotient is correlated with glucose concentration.

4. The apparatus of claim 2, wherein the divisor is a value of a function of dT/dt (f(dT/dt)) that yields a fraction of the substance concentration between 0 and 1 that emits or absorbs photons when taken out of Boltzmann equilibrium at the dT/dt value.

5. The apparatus of claim 1, wherein the calculation of the quotient comprising calculating a slope value for a series of (x,y) values in which x values are the divisor and y values are the dividend measured over time while the surface exhibits the dT/dt.

6. The apparatus of claim 1, wherein the operations further include:
measuring the first measured amount of MIR radiation absorbed by or emitted from the body in the first wavelength at the particular time;
measuring the second measured amount of MIR radiation absorbed by or emitted from the body in the second wavelength at the particular time; and
measuring the measured surface temperature at the particular time.

7. The apparatus of claim 6, wherein the substance has an effect on MIR emission or absorption in the first wavelength and has no or negligible effect on MIR emission or absorption in the second wavelength.

8. The apparatus of claim 7, wherein measuring the first measured amount, the second measured amount, and the measured surface temperature occur during a positive dT/dt (an upward sloping temperature change).

9. The apparatus of claim 8, wherein the operations further include:
normalizing the first measured amount and the second measured amount to black body calibration;
measuring an ambient temperature at the particular time; and
correcting the quotient for ambient temperature effects on a measurement apparatus for the ambient temperature.

10. The apparatus of claim 1, wherein calculating the dT/dt value for the particular time comprises:
measuring the measured surface temperature at each of a plurality of different times including the particular time;
curve-fitting the corresponding plurality of measured surface temperatures to obtain the function for temperature (T) of the surface of the body that varies with time (t), including the particular time;
differentiating the function for temperature (T) to obtain the temperature derivative with respect to time (dT/dt); and
calculating the dT/dt value by evaluating the dT/dt for the particular time.

11. The apparatus of claim 1, wherein the operations further include generating a correlation of the substance concentration with the quotient by:
for each of a plurality of different times, calculating the dT/dt value and calculating the difference;
statistically smoothing the plurality of differences for the corresponding plurality of dT/dt values to correct the plurality of differences;
providing a function of dT/dt (f(dT/dt)) that yields a fraction of the substance concentration between 0 and 1 that emits or absorbs photons when taken out of Boltzmann equilibrium;
for each of the plurality of different times, calculating a f(dT/dt) value by evaluating the f(dT/dt) for the respective dT/dt value and calculating the quotient with the corresponding f(dT/dt) value as the divisor; and
correlating the concentration of the substance in the body with the plurality of quotients.

12. The apparatus of claim 1, further comprising operations including calculating a dT/dt value for the time the MIR radiation is measured.

13. The apparatus of claim 1, wherein the allowing temperature recovery of the surface occurs without the heating or cooling of the element.

14. The apparatus of claim 1, wherein the measured value is correlated with glucose concentration.

15. The apparatus of claim 1, wherein measuring MIR radiation comprises:
measuring MIR radiation during a positive dT/dt (an upward sloping temperature change), the measuring occurring within a first wavelength band in which the substance has an effect on MIR emission; and
measuring reference MIR radiation at the temperature during the positive dT/dt, the measuring occurring within a second wavelength band in which the substance has no or negligible effect on MIR emission.

16. The apparatus of claim 1, wherein the element comprises a ring-shaped heating and/or cooling element and further comprising:
a thermally conductive ring in thermal communication with the ring-shaped heating and/or cooling element; and
a transmission window structure attached to the housing such that a line of sight of the MIR detector passes through the transmission window structure, a surface of the transmission window structure and a surface of the thermally conductive ring being aligned along a same plane outside the housing.

17. The apparatus of claim 16, further comprising a wireless transmitter, the apparatus being configured to send a warning output to a remote device via the wireless transmitter to display a warning, the remote device including a mobile telephone and the warning output indicating that the remote device is to contact an emergency service.

18. The apparatus of claim 1, wherein the element comprises a ring-shaped heating and/or cooling element and further comprising:
a transmission window structure in direct thermal communication with the ring-shaped heating and/or cooling element and attached to the housing such that a line of sight of the MIR detector passes through the transmission window structure.

19. The apparatus of claim 18, wherein the transmission window structure exhibits a thermal conductivity greater than 1,000 Watts/meter-Kelvin.

20. The apparatus of claim 18, further comprising a wireless transmitter, the apparatus being configured to send a warning output to a remote device via the wireless transmitter to display a warning, the remote device including a mobile telephone and the warning output indicating that the remote device is to contact an emergency service.

* * * * *